US00PP16085P3

(12) United States Plant Patent
Knudsen

(10) Patent No.: US PP16,085 P3
(45) Date of Patent: Nov. 1, 2005

(54) ***DAHLIA* PLANT NAMED 'BAHAMAS'**

(50) Latin Name: ***Dahlia* (hybrid)**
Varietal Denomination: Bahamas

(75) Inventor: Jan Skjold Knudsen, Odense (DK)

(73) Assignee: Dalina APS, Odense (DK)

( * ) Notice: Subject to any disclaimer, the term of this patent is extended or adjusted under 35 U.S.C. 154(b) by 0 days.

(21) Appl. No.: 10/808,378

(22) Filed: Mar. 25, 2004

(65) Prior Publication Data

US 2005/0216995 P1 Sep. 29, 2005

(51) Int. Cl.[7] ..... A01H 5/00

(52) U.S. Cl. ..... Plt./321

(58) Field of Search ..... Plt./321

*Primary Examiner*—Kent Bell
(74) *Attorney, Agent, or Firm*—Foley & Lardner, LLP

(57) ABSTRACT

A new and distinct cultivar of *Dahlia* plant named 'Bahamas' characterized by its red ray floret color, RHS 53A; compact plant habit; and vigorous growth habit.

3 Drawing Sheets

Genus and species of the plant claimed: *Dahlia* (hybrid). Variety denomination: 'Bahamas'.

BACKGROUND OF THE INVENTION

The present Invention relates to a new and distinct cultivar of *Dahlia* plant, botanically known as a *Dahlia* (hybrid), and hereinafter referred to by the name 'Bahamas'. The new cultivar 'Bahamas' is a product of a planned breeding program and was selected by the Inventor, Jan Skjold Knudsen, in Fyn, Denmark. The new cultivar 'Bahamas' originated from a cross made by the Inventor between the *Dahlia* cultivar designated 'Borneo' (unpatented) as the female parent and the *Dahlia* cultivar designated 'Lauren' (patented as 'DAPADRED' in the U.S. Plant Pat. No. 11,671) as the male parent.

Asexual reproduction by cuttings of the new variety in Fyn, Denmark has demonstrated that the combination of characteristics as described herein for 'Bahamas' are firmly fixed and are retained through successive generations of asexual reproduction. The new variety reproduces true to type.

BRIEF DESCRIPTION OF THE INVENTION

'Bahamas' has not been tested under all available environmental conditions and the phenotype may vary with variations in environmental conditions such as temperature, light intensity, day length and humidity, without a change in genotype of the plant.

The following traits have been repeatedly observed and are determined to be the unique characteristics of 'Bahamas'. The following characteristics in combination distinguish 'Bahamas' as a new and distinct cultivar:

1. Red ray floret color, RHS 53A;
2. Compact plant habit; and
3. Vigorous growth habit.

Side-by-side comparisons between the new *Dahlia* cultivar 'Bahamas' and the parental cultivars, 'Borneo' and 'Lauren', were conducted by the Inventor in Fyn, Denmark.

Table 1 provides a comparison of plants of 'Bahamas' to plants of the parental cultivars:

TABLE 1

| Characteristic | 'Bahamas' | 'Borneo' | 'Lauren' |
|---|---|---|---|
| Ray floret color | Red, RHS 53A | Red-purple, RHS 70A | Red, RHS 59 A |
| Leaf length | Up to 12 cm | 7–8 cm | About 8.5 cm |

Of the commercial cultivars known to the Inventor, the most similar in comparison to the new *Dahlia* cultivar 'Bahamas' is the female parental cultivar, 'Borneo' (unpatented).

BRIEF DESCRIPTION OF THE DRAWINGS

The accompanying color photographs illustrate the overall appearance and details of inflorescence form color and structures of the new cultivar, showing the colors as true as it is reasonably possible to obtain in color reproductions of this type. Colors in the photographs may differ slightly from the color values cited in the detailed botanical description, which accurately describe the actual colors of the new *Dahlia*.

The first photograph is a side view of a typical flowering plant of 'Bahamas' as grown in an 11 cm pot.

The second photograph is a top view of a typical flowering plant of 'Bahamas'.

The third photograph is a close-up of the inflorescence of 'Bahamas'.

DETAILED BOTANICAL DESCRIPTION

The following observations, measurements and values describe plants grown under commercial conditions. Plants described were 12 to 14 weeks old, and were grown in a greenhouse in Fyn, Denmark with average day temperatures of 18° C. to 25° C., and night temperatures of 16° C. All color references are measured against The Royal Horticultural Society (R.H.S.) Colour Chart. Colors are approximate as color depends on horticultural practices such as light level and treatment rate, among others, without however any variance in genotype.

Plant:

*Form.*—Globular, upright.

*Height.*—17 cm.

*Spread.*—20 cm.

*Natural flowering season.*—Summer to fall.

*Crop time.*—After rooting, about 10–12 weeks are required to produce finished flowering plants in 11 cm pots.

*Plant vigor.*—Vigorous.

*Root structure.*—Fibrous.

*Stem.*—Dark yellow-green, RHS 144; glabrous; diameter 10–12 mm.

*Lateral branches.*—10 in quantity; 7–10 mm diameter; 10 cm in length (including inflorescence); color: yellow-green, RHS 144.

*Internode length.*—3 cm.

Foliage:

*Leaves.*—Quantity: 4–5 pairs per lateral branch.

*Arrangement.*—Opposite, decussate.

*Length.*—Up to 12 cm.

*Width.*—5–6 cm.

*Shape.*—Elliptical, acuminate tip, decurrent base, crenate margin.

*Texture.*—Glabrous.

*Color.*—Young leaf upper side green RHS 136A; young leaf under side gray-green RHS 189C; mature leaf upper side RHS 134A; mature leaf under side RHS 189C.

*Venation.*—Upper side RHS 135C; under side RHS 144A.

*Petiole.*—2 cm length, 5–8 mm diameter, color RHS 144A.

Inflorescence:

*Arrangement.*—Composite inflorescences in leaf axils.

*Inflorescence type.*—Capitulum.

*Inflorescence height.*—2–3 cm.

*Inflorescence width.*—6 cm.

*Flowering habit.*—Upright.

*Quantity of inflorescences.*—2–3 per lateral stem.

*Inflorescence longevity.*—7 days on the plant.

Bud:

Quantity.—2–3 per lateral stem (buds continue to develop when dead inflorescences are removed).

*Shape.*—Globular.

*Size.*—Up to 2 cm in length, 1 cm diameter.

*Color.*—RHS 144C.

Florets:

*Shape.*—Disc, tubular to single floret (lanceolate to rounded tip); ray, single fused floret (oval and slightly involuate to rounded tip).

*Number.*—About 20 disc florets and 70 ray florets per capitulum (depending on light and temperature conditions).

*Length.*—Disc 2 mm; ray 25–30 mm.

*Width.*—Disc 2 mm; ray 15 mm.

*Diameter.*—Disc 2–3 mm.

*Margin.*—Disc and ray, entire.

*Color.*—Disk, yellow, RHS 13A at the apical end fading into yellow-white, RHS 158C; ray, young upper side: red-purple, between RHS 72B to 72C, mature upper side, red, RHS 53A with gray-purple, RHS 184C at base mature under side, red-purple, RHS 61A to 61B.

Phyllaries:

*Quantity.*—Leaf-like, about 5–6; Scale-like, about 60.

*Shape.*—Leaf-like, oval with rounded tip and fused base; scale-like, oval with acute tip and fused base.

*Length.*—Leaf-like, 12 mm; scale-like, 25 mm.

*Width.*—Leaf-like, 6 mm; scale-like, 5 mm.

*Color.*—Leaf-like, immature upper side, green, RHS 138A; immature under side, green, RHS 143D; mature upper side, green, RHS 137C; mature under side, gray-green, RHS 191B; scale-like, immature upper side, translucent, yellow-green, RHS 149B; immature under side, stripes of green, RHS 143A; mature upper side, yellow-green, RHS 144C; mature under side, gray-green, RHS 143A.

Calyx: 3 mm length, 14 mm diameter.

Peduncle: 5 cm length, 3 mm diameter; strength: strong; color young, yellow-green, RHS 144B, to old, gray-brown, RHS 199A.

Reproductive organs:

Androecium:

*Location.*—Disc florets only.

*Anthers.*—5 mm in length, RHS 23B.

*Pollen.*—RHS 14A.

Gynoecium:

*Location.*—Disc florets.

*Pistils.*—1 per disc floret, 15 mm length.

*Stigma.*—RHS 14A.

*Style.*—1 cm length, RHS 1B.

*Ovary.*—RHS 150B.

Temperature tolerance: High tolerance to 35° C.; low tolerance to 0° C.

I claim:

1. A new and disctinct cultivar of *Dahlia* plant named 'Bahamas', as described and illustrated herein.

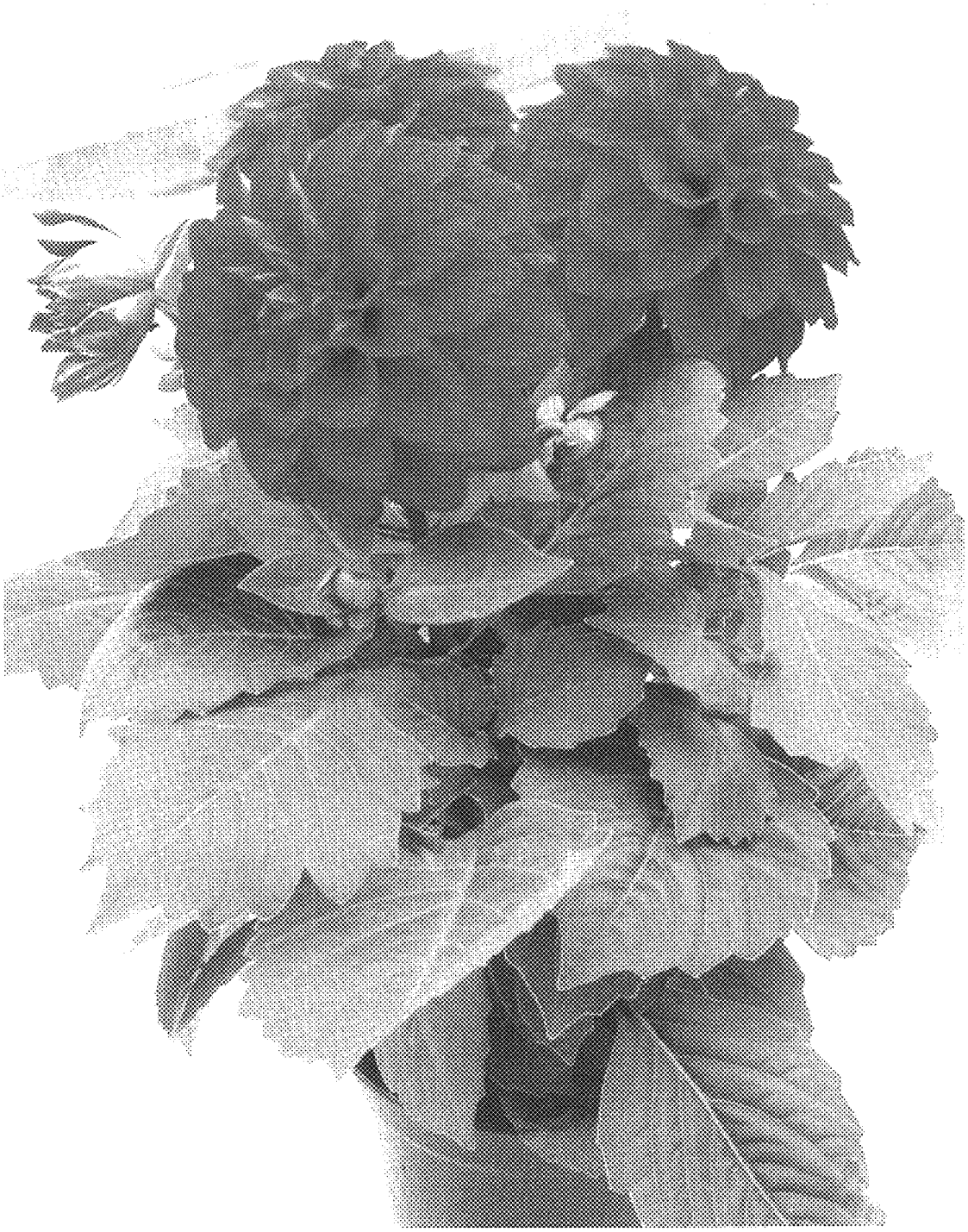

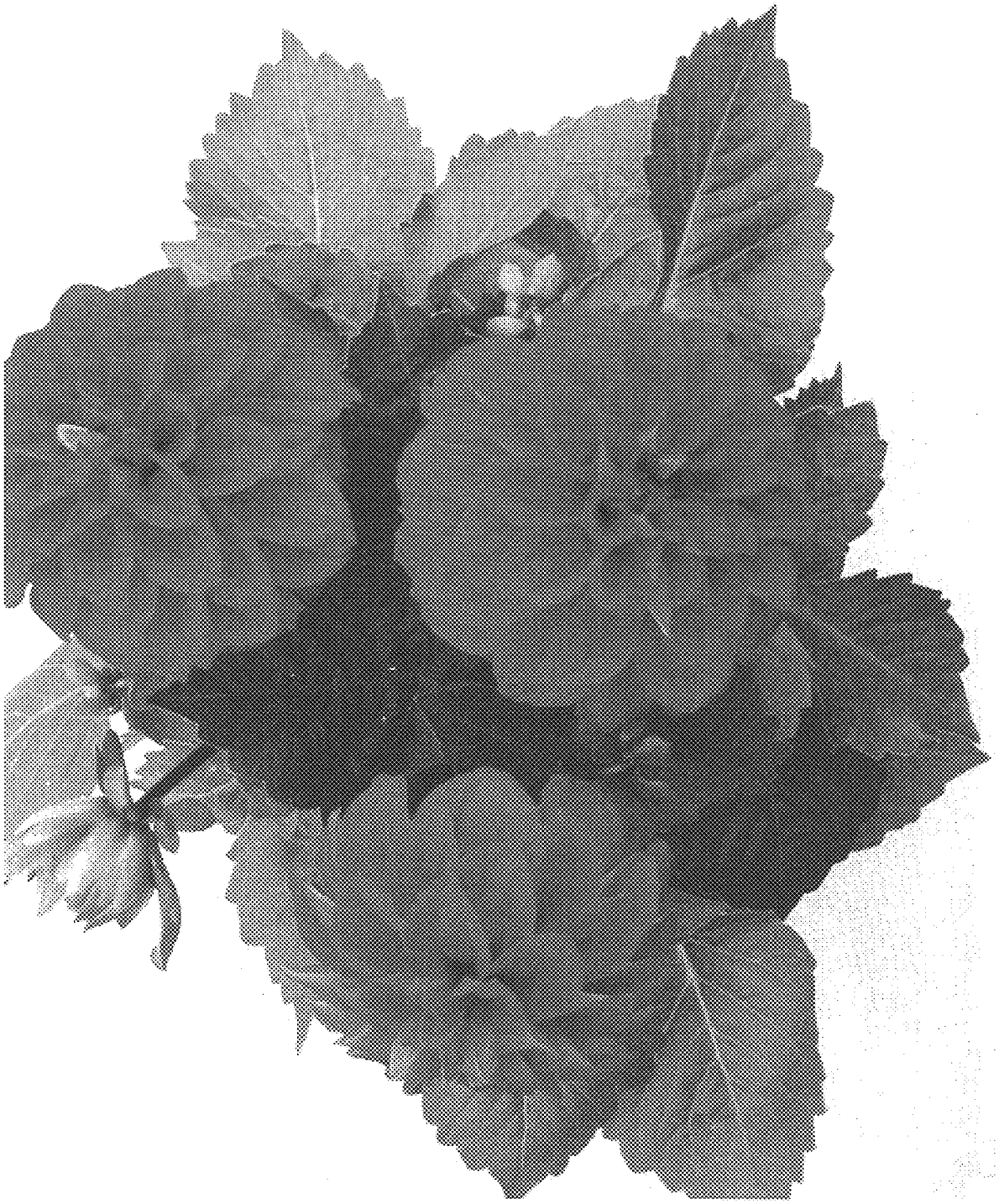

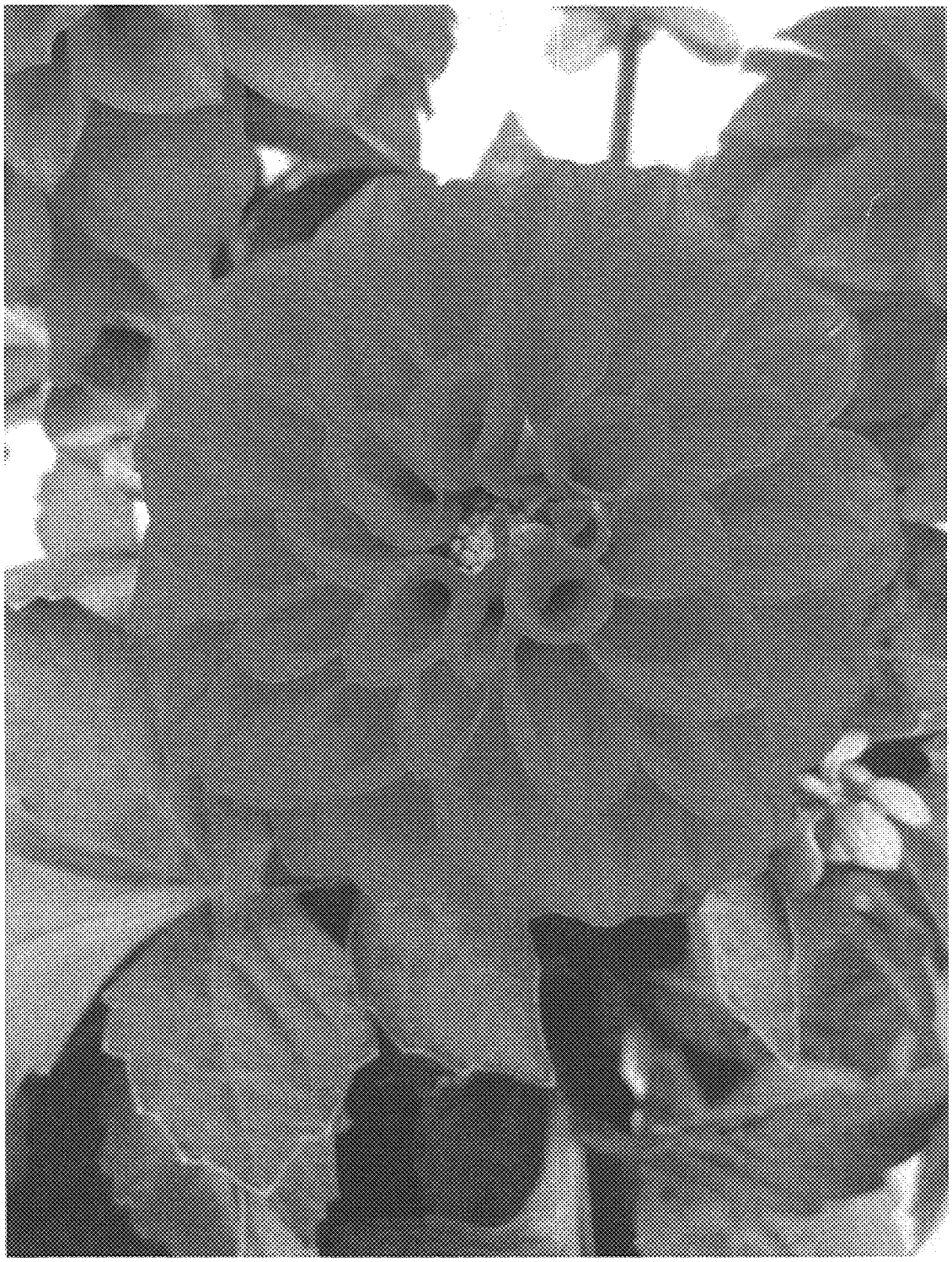

* * * * *